US011224743B2

(12) United States Patent
Govea et al.

(10) Patent No.: US 11,224,743 B2
(45) Date of Patent: Jan. 18, 2022

(54) SYSTEMS AND METHODS FOR MAKING AND USING MODULAR LEADS FOR ELECTRICAL STIMULATION SYSTEMS

(71) Applicant: Boston Scientific Neuromodulation Corporation, Valencia, CA (US)

(72) Inventors: Michael X. Govea, Castaic, CA (US); Joshua Dale Howard, Sacramento, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 229 days.

(21) Appl. No.: 16/573,316

(22) Filed: Sep. 17, 2019

(65) Prior Publication Data

US 2020/0094047 A1    Mar. 26, 2020

Related U.S. Application Data

(60) Provisional application No. 62/734,386, filed on Sep. 21, 2018.

(51) Int. Cl.
*A61N 1/05* (2006.01)
*A61N 1/08* (2006.01)

(52) U.S. Cl.
CPC ............ *A61N 1/0504* (2013.01); *A61N 1/086* (2017.08)

(58) Field of Classification Search
CPC ..... A61N 1/0504; A61N 1/0551; A61N 1/086
USPC ......................................................... 607/148
See application file for complete search history.

(56) References Cited

U.S. PATENT DOCUMENTS

| 5,076,270 A | 12/1991 | Stutz, Jr. |
| 5,437,193 A | 8/1995 | Schleitweiler et al. |
| 5,445,608 A | 8/1995 | Chen et al. |
| 5,556,421 A | 9/1996 | Prutchi et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |

(Continued)

FOREIGN PATENT DOCUMENTS

| WO | 02/091935 | 11/2002 |
| WO | 2011/031131 | 3/2011 |

(Continued)

OTHER PUBLICATIONS

Baxter, G.D. et al., Effects of Low Intensity Infrared Laser Irradiation Upon Conduction in the Human Median Nerve In Vivo, Experimental Physiology (1994) 79, 227-234.

(Continued)

*Primary Examiner* — Carl H Layno
*Assistant Examiner* — Jane C Kalinock
(74) *Attorney, Agent, or Firm* — Branch Partners PLLC; Bruce E. Black

(57) ABSTRACT

An implantable electrical stimulation lead includes at least three modular lead elements configured to couple together to form the lead, each of the modular lead elements including a proximal end portion, a distal end portion, and a male connector element or a female connector element disposed on at least one of the proximal end portion or the distal end portion of the modular lead element, The modular lead elements are coupleable together by insertion of a male connector element into a female connector element.

20 Claims, 7 Drawing Sheets

(56) References Cited

U.S. PATENT DOCUMENTS

| | | |
|---|---|---|
| 6,295,944 B1 | 10/2001 | Lovett |
| 6,364,278 B1 | 4/2002 | Lin et al. |
| 6,391,985 B1 | 5/2002 | Goode et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,244,150 B1 | 7/2007 | Brase et al. |
| 7,288,108 B2 | 10/2007 | DiMauro et al. |
| 7,395,118 B2 | 7/2008 | Erickson |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,946,980 B2 | 5/2011 | Reddy et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,386,054 B2 | 2/2013 | North |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,525,027 B2 | 9/2013 | Lindner et al. |
| 8,571,665 B2 | 10/2013 | Moffitt et al. |
| 8,600,509 B2 | 12/2013 | McDonald et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,849,632 B2 | 9/2014 | Sparks et al. |
| 8,936,630 B2 | 1/2015 | Denison et al. |
| 8,958,615 B2 | 2/2015 | Blum et al. |
| 9,238,132 B2 | 1/2016 | Barker |
| 9,415,154 B2 | 8/2016 | Leven |
| 9,421,362 B2 | 8/2016 | Seeley |
| 9,550,063 B2 | 1/2017 | Wolf, II |
| 9,643,010 B2 | 5/2017 | Ranu |
| 9,681,809 B2 | 6/2017 | Sharma et al. |
| 2002/0156513 A1 | 10/2002 | Borkan |
| 2002/0161417 A1 | 10/2002 | Scribner |
| 2005/0216072 A1 | 9/2005 | Mahadevan-Jansen et al. |
| 2006/0129210 A1 | 6/2006 | Cantin et al. |
| 2006/0155348 A1 | 7/2006 | deCharms |
| 2006/0161227 A1 | 7/2006 | Walsh, Jr. et al. |
| 2007/0053996 A1 | 3/2007 | Boyden et al. |
| 2007/0150036 A1 | 6/2007 | Anderson |
| 2007/0161919 A1 | 7/2007 | DiLorenzo |
| 2007/0244526 A1 | 10/2007 | Zaghetto et al. |
| 2008/0046053 A1 | 2/2008 | Wagner et al. |
| 2008/0077198 A1 | 3/2008 | Webb et al. |
| 2008/0167701 A1* | 7/2008 | John ............... A61N 1/05 607/116 |
| 2008/0197300 A1 | 8/2008 | Kayser et al. |
| 2008/0243218 A1* | 10/2008 | Bottomley ......... A61N 1/086 607/116 |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2010/0076508 A1 | 3/2010 | McDonald et al. |
| 2010/0076535 A1 | 3/2010 | Pianca et al. |
| 2010/0094364 A1 | 4/2010 | McDonald |
| 2010/0114190 A1 | 5/2010 | Bendett et al. |
| 2010/0174344 A1 | 7/2010 | Dadd et al. |
| 2010/0256693 A1 | 10/2010 | McDonald et al. |
| 2010/0268298 A1 | 10/2010 | Moffitt et al. |
| 2010/0292758 A1 | 11/2010 | Lee et al. |
| 2010/0324630 A1 | 12/2010 | Lee et al. |
| 2010/0326701 A1 | 12/2010 | McDonald |
| 2011/0004267 A1 | 1/2011 | Meadows |
| 2011/0005069 A1 | 1/2011 | Pianca |
| 2011/0009932 A1 | 1/2011 | McDonald et al. |
| 2011/0046432 A1 | 2/2011 | Simon et al. |
| 2011/0046700 A1 | 2/2011 | McDonald et al. |
| 2011/0078900 A1 | 4/2011 | Pianca et al. |
| 2011/0125077 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0253261 A1 | 10/2012 | Poletto et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0102861 A1 | 4/2013 | Oki et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0304152 A1 | 11/2013 | Bradley et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067023 A1 | 3/2014 | Register et al. |
| 2014/0122379 A1 | 5/2014 | Moffitt et al. |
| 2014/0142664 A1 | 5/2014 | Roukes et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0306414 A1 | 10/2015 | Nielsen et al. |
| 2015/0375006 A1 | 12/2015 | Denison et al. |
| 2016/0030749 A1 | 2/2016 | Carcieri et al. |
| 2016/0228692 A1 | 8/2016 | Steinke et al. |
| 2016/0271392 A1 | 9/2016 | Vallejo et al. |
| 2016/0287885 A1 | 10/2016 | Saini |
| 2016/0346557 A1 | 12/2016 | Bokil |
| 2016/0375258 A1 | 12/2016 | Steinke |
| 2017/0061627 A1 | 3/2017 | Bokil |
| 2017/0100580 A1 | 4/2017 | Olson |
| 2017/0136254 A1 | 5/2017 | Simon et al. |

(56) References Cited

U.S. PATENT DOCUMENTS

| | | |
|---|---|---|
| 2017/0225007 A1 | 8/2017 | Orinski |
| 2017/0259078 A1 | 9/2017 | Howard |
| 2017/0281966 A1 | 10/2017 | Basiony |
| 2017/0304633 A1 | 10/2017 | Zhang |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1 | 6/2018 | Chabrol et al. |
| 2018/0193655 A1 | 7/2018 | Zhang et al. |
| 2018/0256906 A1 | 9/2018 | Pivonka et al. |
| 2018/0369606 A1 | 12/2018 | Zhang et al. |
| 2018/0369607 A1 | 12/2018 | Zhang et al. |
| 2019/0209834 A1 | 7/2019 | Zhang et al. |
| 2019/0209849 A1 | 7/2019 | Hershey et al. |
| 2020/0094047 A1 | 3/2020 | Govea et al. |
| 2020/0155854 A1 | 5/2020 | Leven et al. |
| 2020/0376262 A1 | 12/2020 | Clark et al. |

FOREIGN PATENT DOCUMENTS

| | | |
|---|---|---|
| WO | 2011150430 | 12/2011 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |

OTHER PUBLICATIONS

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler; Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results In Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

* cited by examiner

SYSTEMS AND METHODS FOR MAKING AND USING MODULAR LEADS FOR ELECTRICAL STIMULATION SYSTEMS

CROSS-REFERENCE TO RELATED APPLICATIONS

This application claims the benefit under 35 U.S.C. § 119(e) of U.S. Provisional Patent Application Ser. No. 62/734,386, filed Sep. 21, 2018, which is incorporated herein by reference.

FIELD

The present disclosure is directed to the area of implantable electrical stimulation systems and methods of making and using the systems. The present disclosure is also directed to implantable electrical stimulation leads having modular lead elements with different properties, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

One aspect is an implantable electrical stimulation lead that includes at least three modular lead elements configured to couple together to form the lead, each of the modular lead elements including a proximal end portion, a distal end portion, and a male connector element or a female connector element disposed on at least one of the proximal end portion or the distal end portion of the modular lead element, The modular lead elements are coupleable together by insertion of a male connector element into a female connector element. Each of the modular lead elements includes contacts disposed on each male connector element or within each female connector element of the modular lead element and conductors extending along the modular lead element from the contacts. The conductors of at least one of the modular lead elements are disposed in a low impedance arrangement. The conductors of at least one of the modular lead elements are disposed in a high impedance arrangement.

In at least some aspects, the low impedance arrangement of the conductors includes the conductors extending along the modular lead element in either a straight configuration or a twisted configuration with twisting of the conductors at a rate of no more than one turn per centimeter or no more than 0.8, 0.5, 0.4, or 0.2 turns per centimeter. In at least some aspects, the high impedance arrangement of the conductors extending along the modular lead element in a coiled configuration with a coil pitch of more than one turn per centimeter or at least two, three, four, five, eight, ten, or more turns per centimeter. In at least some aspects, the high impedance arrangement of the conductors forms at least one suppression unit. In at least some aspects, each of the at least one suppression units includes a first conductor segment extending in a first direction along a longitudinal length of the modular lead element from a beginning point to a first position; a second conductor segment extending from the first position in a second direction, opposite the first direction, to a second position; and a third conductor segment extending in the first direction from the second position to an endpoint. In at least some aspects, at least one of the first conductor segment, the second conductor segment, or the third conductor segment is coiled.

In at least some aspects, the at least three modular lead elements includes a first modular lead element including a plurality of terminals disposed along the proximal end portion, a first male connector element or female connector element disposed on the distal end portion, and conductors extending from the terminals to the contacts of the first male connector element or female connector element, a second modular lead element including a plurality of electrodes disposed along the distal end portion, a second male connector element or female connector element disposed on the proximal end portion, and conductors extending from the electrodes to the contacts of the second male connector element or female connector element, and a third modular lead element including a third male connector element or female connector element disposed along the distal end portion, a fourth male connector element or female connector element disposed on the distal end portion, and conductors extending from the contacts of the third male connector element or female connector element to the contacts of the fourth male connector element or female connector element. In at least some aspects, the third modular lead element has the conductor disposed in the high impedance arrangement and the first and second modular lead elements have the conductors disposed in the low impedance arrangement.

Another aspect is an implantable electrical stimulation lead that includes at least three modular lead elements configured to couple together to form the lead, each of the modular lead elements including a proximal end portion, a distal end portion, and a male connector element or a female connector element disposed on at least one of the proximal end portion or the distal end portion of the modular lead element. The modular lead elements are coupleable together by insertion of a male connector element into a female connector element. Each of the modular lead elements includes contacts disposed on each male connector element or within each female connector element of the modular lead element and conductors extending along the modular lead element from the contacts. The conductors of at least one of the modular lead elements have a first conductor arrangement in which, starting from the proximal end portion, the conductors extend along the modular lead element from the proximal end portion to the distal end portion without reversing direction back towards the proximal end portion. The conductors of at least one of the modular lead elements have a second conductor arrangement in which, starting from the proximal end portion, the conductors extend along the modular lead element from the proximal end portion to the distal end portion with at least one reversal of direction back towards the proximal end portion followed by a resumption in the direction towards the distal end portion.

In at least some aspects, the at least three modular lead elements includes a first modular lead element including a plurality of terminals disposed along the proximal end portion, a first male connector element or female connector element disposed on the distal end portion, and conductors extending from the terminals to the contacts of the first male connector element or female connector element, a second modular lead element including a plurality of electrodes disposed along the distal end portion, a second male connector element or female connector element disposed on the proximal end portion, and conductors extending from the electrodes to the contacts of the second male connector element or female connector element, and a third modular lead element including a third male connector element or female connector element disposed along the distal end portion, a fourth male connector element or female connector element disposed on the distal end portion, and conductors extending from the contacts of the third male connector element or female connector element to the contacts of the fourth male connector element or female connector element. In at least some aspects, the third modular lead element has the conductors disposed in the second conductor arrangement and the first and second modular lead elements have the conductors disposed in the first conductor arrangement. In at least some aspects, the second conductor arrangement forms at least one suppression unit. In at least some aspects, each of the at least one suppression units includes a first conductor segment extending in a first direction along a longitudinal length of the modular lead element from a beginning point to a first position; a second conductor segment extending from the first position in a second direction, opposite the first direction, to a second position; and a third conductor segment extending in the first direction from the second position to an endpoint.

In at least some aspects of nay of the implantable electrical stimulation lead described above, each female connector element includes an outer helix of tubes and each male connector element includes an outer helix of tubes and an inner helix of tubes, wherein the inner helix of tubes is configured to screw into to outer helix of tubes of the female connector element to mate the female connector unit to the male connector element.

In at least some aspects of nay of the implantable electrical stimulation lead described above, each female connector element has an outer diameter no greater than an outer diameter of the modular lead element, of which the female connector element is part, exclusive of all of the female or male connector elements of the modular lead element.

Yet another aspect is an electrical stimulation system that includes any of the implantable electrical stimulation leads described above; and a control module coupleable to the implantable electrical stimulation lead and including a housing and an electronic subassembly disposed in the housing and electrically coupleable to the lead.

A further aspect is a method of making any of the implantable electrical stimulation leads described above. The method includes coupling the at least three modular lead elements together by inserting the female connector elements into the male connector elements.

In at least some embodiments, the method further includes selecting the at least three modular lead elements based on patient anatomy. In at least some embodiments, coupling the at least modular lead elements includes at least one of: i) coupling a modular lead element with conductors in a high impedance arrangement immediately proximal to a modular lead element comprising a plurality of electrodes; ii) coupling a modular lead element with conductors in a high impedance arrangement immediately distal to a modular lead element comprising a plurality of terminals; iii) coupling a modular lead element with conductors in a high impedance arrangement immediately proximal to a modular lead element that is arranged for insertion through a size-restricted anatomical region; iv) coupling a modular lead element with conductors in the high impedance arrangement at a position along the lead intended for implantation adjacent to neural tissue; or v) coupling a modular lead element with conductors in the high impedance arrangement at a position along the lead intended for implantation adjacent to fatty tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable electrical stimulation systems and methods of making and using the systems. The present disclosure is also directed to implantable electrical stimulation leads having modular lead elements with different properties, as well as methods of making and using the leads and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead may be exemplified, but it will be understood that the methods and systems described herein are also applicable to paddle leads and other leads.

Figure 1:
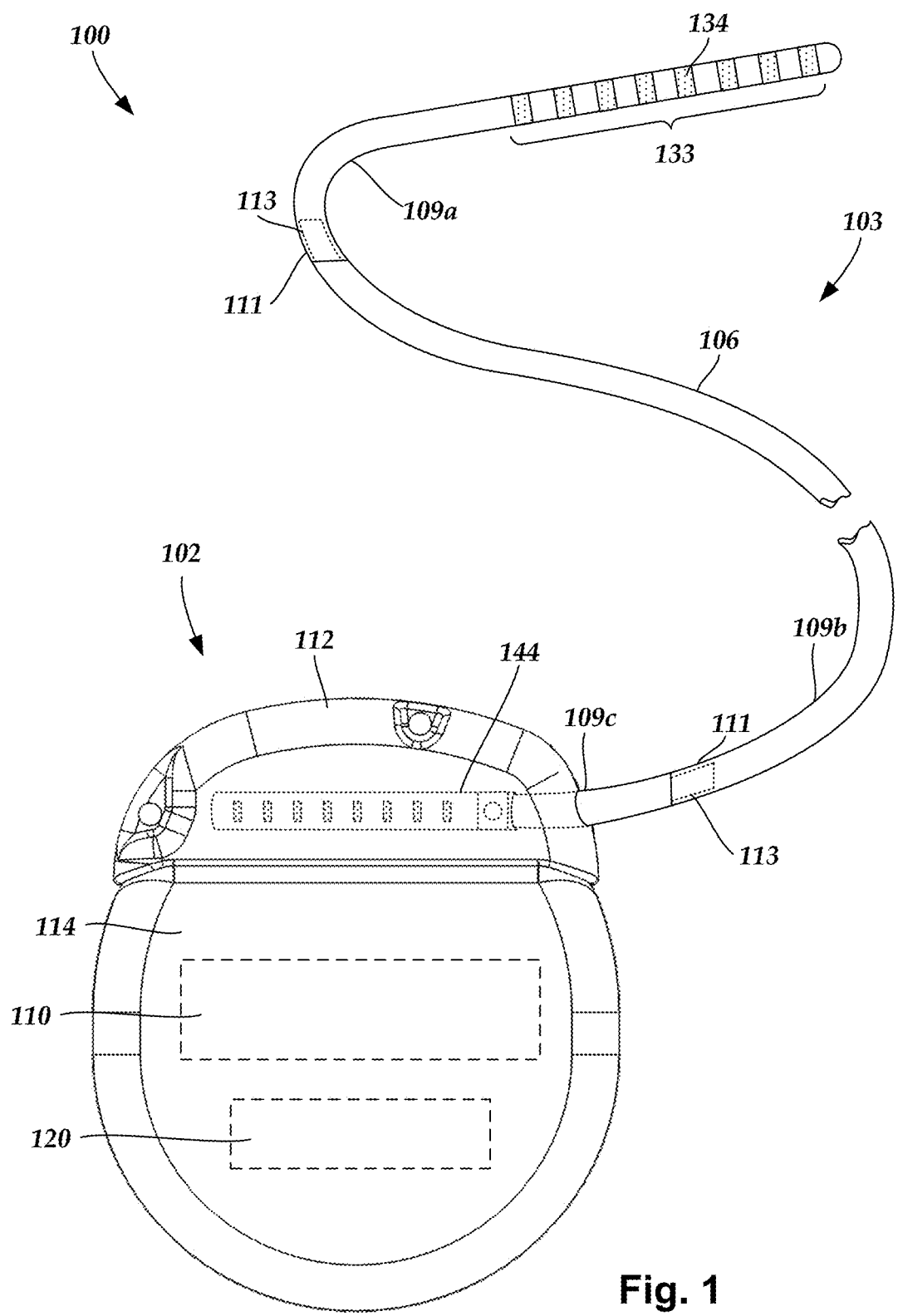
FIG. 1 is a schematic view of one embodiment of an electrical stimulation system that includes a percutaneous lead body coupled to a control module.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 is a percutaneous lead and includes a lead body 106. In at least some embodiments, the lead 103 is isodiametric along a longitudinal length of the lead body 106. An array 133 of electrodes, such as electrodes 134, is disposed along the distal end portion of the lead body 106 and an array of terminals (e.g., 310 in FIG. 3A-3B) is disposed along the proximal end portion of the lead body. In FIG. 1, the lead 103 is shown having a single lead body 106. It will be understood that the lead 103 can include any suitable number of lead bodies including, for example, one, two, three, four, five, six, seven, eight or more lead bodies 106 (see, for example, FIG. 2).

The lead body 106 of the illustrated embodiment of FIG. 1 is formed of modular lead elements 109a, 109b, 109c that fit together with each of the modular lead elements having at least one female connector element 111 or male connector element 113 disposed on at least one end of the modular lead element. Each female connector element 111 has a lumen for receiving a male connector element 113. A modular lead element 109a, 109c at either end of the lead body can include either a female connector element 111 or male connector element 113 at the end that joins to another modular lead element 109b. For a modular lead element 109b that is intermediate between two other modular lead elements 109a, 109c, each end can include either a female connector element 111 or a male connector element 113. In at least some embodiments, an intermediate modular lead element 109b may include a female connector element 111 at one end and a male connector element 113 at another end. In other embodiments, an intermediate modular lead element 109b may include either female connector elements 111 at both ends or male connector elements 113 at both ends.

Forming a lead body 106 with modular lead elements 109a, 109b, 109c permits the creation of a lead with one or more different electrical, mechanical, or other properties along its length. As an example, terminal modular lead elements 109a, 109b can be made with low impedance conductor arrangements to facilitate transfer of electrical energy from terminals or electrodes along the lead. Lower impedance modular lead element may also have lower power consumption and produce less waveform distortion.

In some embodiments, an intermediate modular lead element 109c (or any other modular lead element) may have a conductor arrangement having a higher impedance, for example, a higher impedance at relatively high frequency (as compared to the frequency of the stimulation pulses) to reduce or prevent current induced in the lead by RF and time-varying magnetic field gradients during an MIll procedure. For example, the intermediate modular lead element 109c (or other modular lead element) may provide at least some protection from induced current during an MIll procedure and may also provide heat dissipation of the induced current at positions along the lead that are separated from the electrodes 134 or control module 102. In at least some embodiments, the higher impedance modular lead element may be placed along the lead at regions of the lead or anatomy (when the lead is implanted) that are less critical, less susceptible to heat, or more tolerant of heating.

Additionally or alternatively, modular lead elements can be used to create leads with different lengths, different electrode or terminal configurations, different numbers of lead bodies, or the like by using different combinations and selections of modular lead elements.

Figure 2:
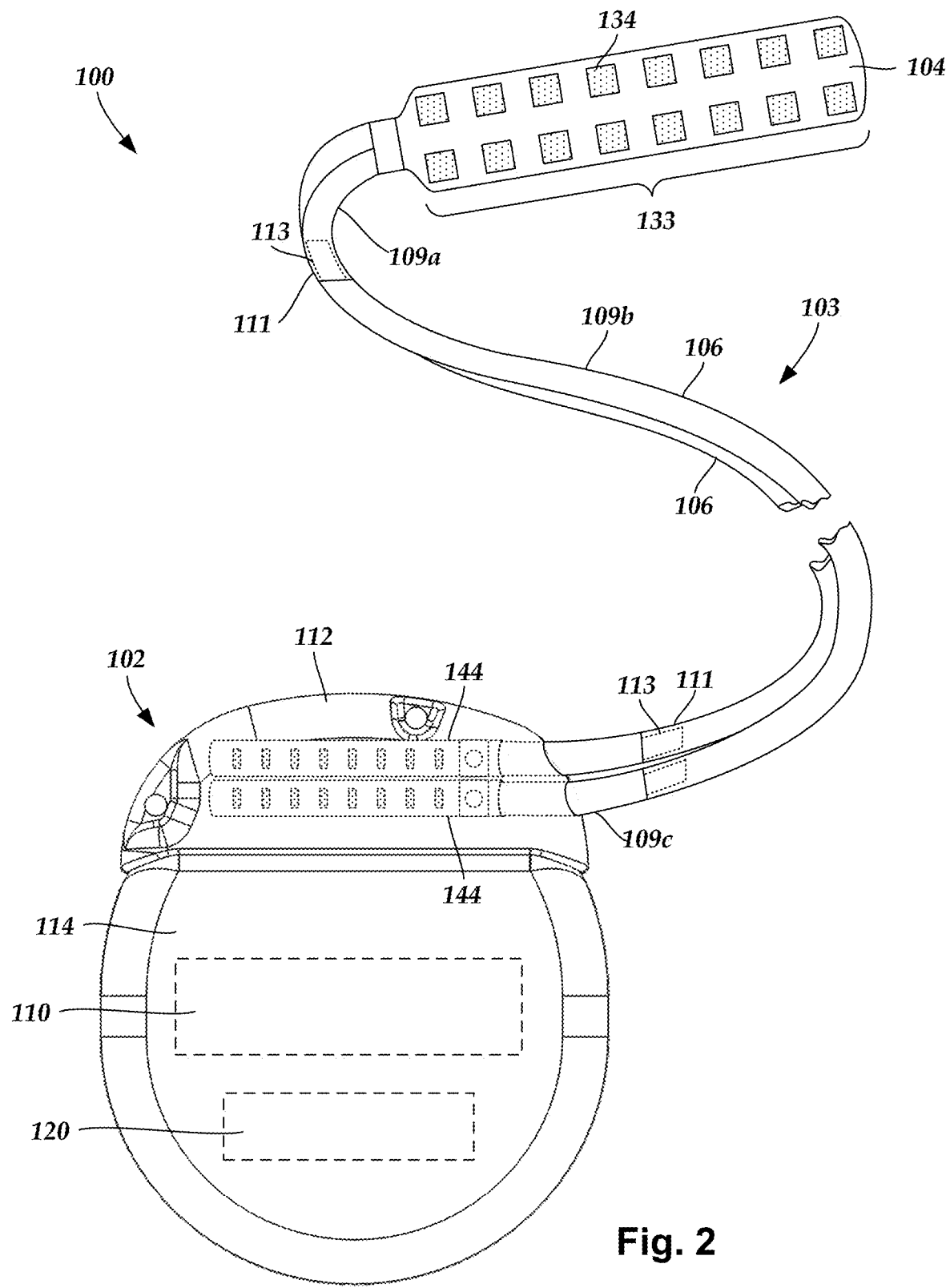
FIG. 2 is a schematic view of another embodiment of an electrical stimulation system that includes a paddle body coupled to a control module.

FIG. 2 illustrates schematically another embodiment of an electrical stimulation system 100, where the lead 103 is a paddle lead and includes a paddle body 104 and one or more lead bodies 106. An array 133 of electrodes, such as electrode 134, is disposed on the paddle body 104, and an array of terminals (e.g., 310 in FIG. 3A-3B) is disposed along each of the one or more lead bodies 106. Each of the lead bodies 106 is formed of modular lead elements 109a, 109b, 109c that fit together with each of the modular lead elements having at least one female connector element 111 or male connector element 113 disposed on at least one end of the modular lead element, as described above.

In at least some embodiments of a lead with multiple lead bodies, the electrical stimulation system 100 can have a splitter (not shown). The splitter includes a splitter connector configured to couple to a proximal end of the lead 103, and one or more splitter tails configured and arranged to couple to the control module 102 (or another splitter, a lead extension, an adaptor, or the like). Examples of a splitter can be found in references cited above as well as U.S. Pat. Nos. 8,600,509; 9,238,132; and 9,643,010, all of which are incorporated herein by reference.

The lead 103 can be coupled to the control module 102 in any suitable manner. In FIGS. 1 and 2, the lead 103 is shown coupling directly to the control module 102. In at least some other embodiments, the lead 103 couples to the control module 102 via one or more intermediate devices. For example, in at least some embodiments one or more lead extensions can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In at least some embodiments, the control module 102 includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the lead 103 and the control module 102, may be implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 2, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, or the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
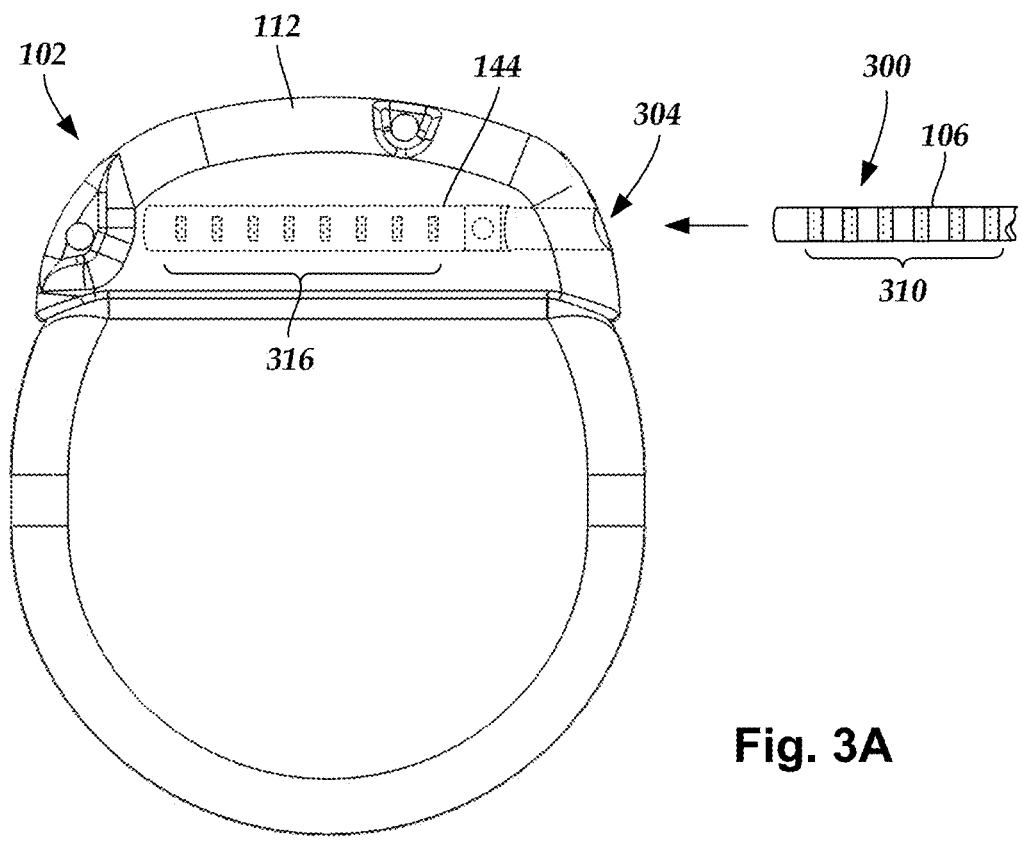
FIG. 3A is a schematic view of one embodiment of a connector assembly disposed in the control module, the connector assembly configured and arranged to receive the proximal portion of one of the lead bodies of FIGS. 1-2.
Figure 3B:
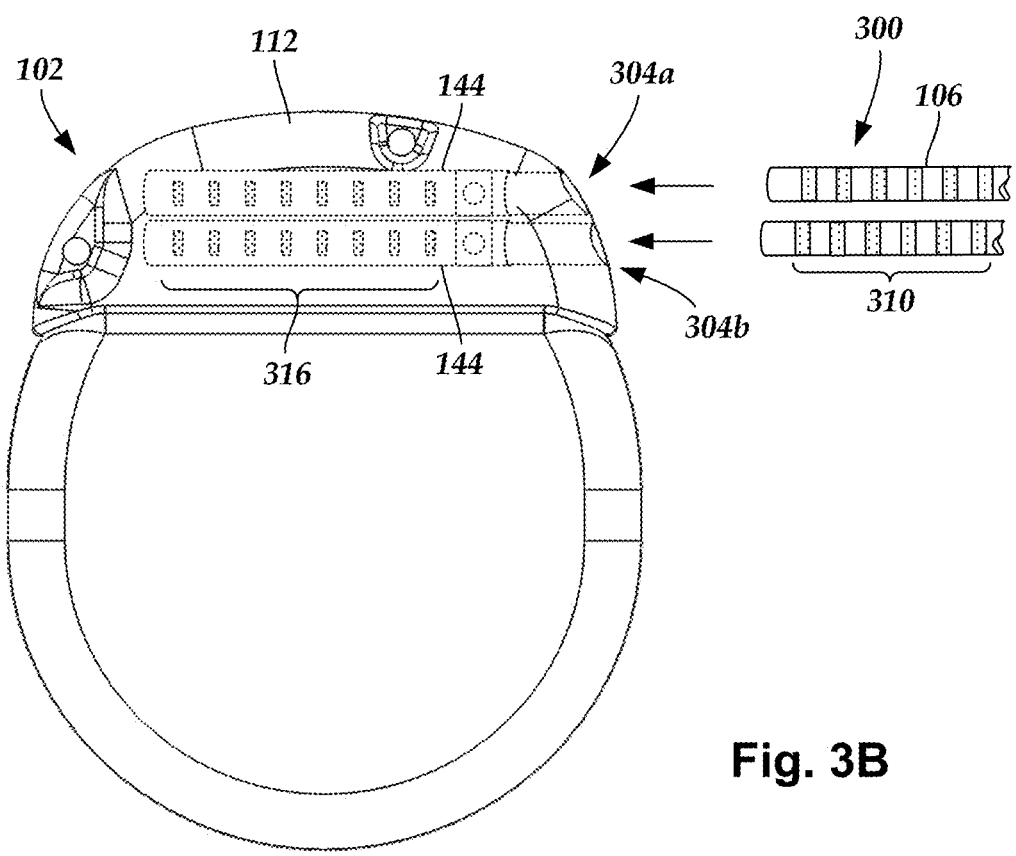
FIG. 3B is a schematic view of one embodiment of a plurality of connector assemblies disposed in the control module, the connector assemblies configured and arranged to receive the proximal portions of the lead bodies of FIGS. 1-2.

FIGS. 3A and 3B are schematic side views of two embodiment of a proximal end of one or more elongated devices 300 configured and arranged for coupling to one embodiment of the control module connector 144. The one or more elongated devices may include, for example, one or more of the lead bodies 106 of FIGS. 1 and 2, one or more intermediate devices (e.g., a splitter, a lead extension, an adaptor, or the like or combinations thereof), or a combination thereof.

As illustrated in FIGS. 3A and 3B, terminals 310 are typically disposed along the proximal end of the one or more lead bodies 106 of the electrical stimulation system 100 (as well as any splitters, lead extensions, adaptors, or the like) for electrical connection to corresponding connector contacts 316. The connector contacts are disposed in connectors 144 which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The control module connector 144 defines at least one port into which a proximal end of the elongated device 300 can be inserted, as shown by directional arrow(s). In FIG. 3A (and in other figures), the control module connector 144 is shown having one port 304 and the control module connector 144 in FIG. 3B is shown having two ports 304a and 304b. The control module connector 144 can define any suitable number of ports including, for example, one, two, three, four, five, six, seven, eight, or more ports.

The control module connector 144 also includes a plurality of connector contacts, such as connector contact 316, disposed within each port 304a and 304b. When the elongated device 300 is inserted into the ports 304a and 304b, the connector contacts 316 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, all of which are incorporated herein by reference.

FIGS. 1, 2, 3A, and 3B illustrate embodiments of at least some components of an electrical stimulation system. It will be understood that the electrical stimulation system can include more, fewer, or different components and can have a variety of different configurations including those configurations disclosed in the electrical stimulation system references cited herein.

As described above, the lead 103 can be formed using modular lead elements 109a, 109b, 109c, as illustrated in FIGS. 1 and 2. Any suitable number of modular lead elements can be used including, but not limited to, two, three, four, five, six, eight, ten, or more modular lead elements. The modular lead elements can be coupled together by insertion of a male connector element 113 into a female connector element 111, as illustrated in FIGS. 1 and 2. In some embodiments, the modular lead elements can be coupled together by the manufacturer. In other embodiments, the modular lead elements may be sold uncoupled and can be assembled by a clinician or other individual.

In at least some embodiments, one or more of the modular lead elements may be low impedance modular lead elements with electrically conductive wires ("conductors") disposed in a low impedance arrangement and extending along the modular lead element. The conductors typically have an insulator disposed around the metal wire. As examples of low impedance arrangements, the conductors can extend along the modular lead element in a straight arrangement or in a twisted arrangement with a twist of no more than 1, 0.8, 0.5, 0.4, 0.3, 0.2, or 0.1 turns per centimeter. It will be understood, however, that this twisting refers to a conductor as a whole. The individual conductors can be single filar or contain multiple filars including multiple filars that are twisted or coiled around each other; however, such twisting or coiling of the individual filars does not indicate whether the conductor itself is in the twisted arrangement described above.

In other embodiments, a low impedance modular lead element can include the conductors arranged so that, starting from the proximal end portion, the conductors extend along the modular lead element from the proximal end portion to the distal end portion without reversing direction back towards the proximal end portion.

In at least some embodiments, the conductors can be embedded in the non-conductive material of the lead body 106 or can be disposed in one or more lumens extending along the lead body 106. In some embodiments, there is an individual lumen for each conductor. In other embodiments, two or more conductors extend through a lumen.

Figure 4:
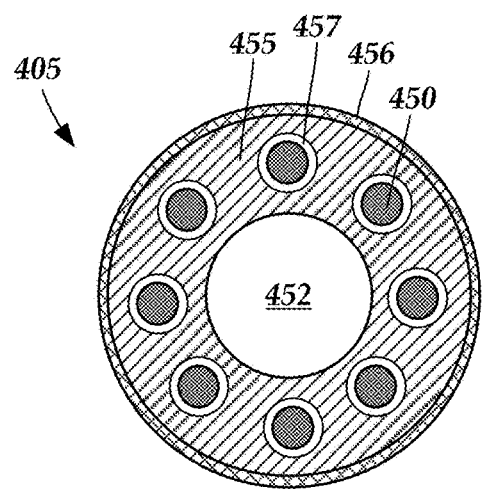
FIG. 4 is a schematic cross-section of one embodiment of a modular lead element with a multi-lumen conductor guide.

FIG. 4 illustrates a cross-section of one embodiment of a low impedance modular lead element 409 of a lead. The low impedance modular lead element 409 includes a non-conductive jacket 456 and a non-conductive, multi-lumen conductor guide 455 with a central lumen 452 and multiple conductor lumens 457 disposed around the central lumen. At least some of the conductor lumens 457 include one or more conductors 450 disposed therein. The central lumen 452 (or another lumen) may be open at the proximal end of the modular lead element 409 for inserting a stylet to facilitate placement of the lead within a body of a patient or for infusing drugs or medications through the lead. The central lumen (or another lumen) may be open at, or near, the distal end of the modular lead element so that the stylet may extend to the next modular lead element or for infusion of drugs or medication into the site of implantation of the lead. In at least some embodiments, the one or more lumens are permanently sealed, or removably sealable, at the distal end.

In at least some embodiments, one or more of the modular lead elements may be high impedance modular lead elements with electrically conductive wires ("conductors") disposed in a high impedance arrangement and extending along the modular lead element. The conductors typically have an insulator disposed around the metal wire. As an example of a high impedance arrangement, the conductors can be coiled conductors extending along the modular lead element to increase the impedance of the modular lead element.

In at least some embodiments, a high impedance modular lead element may, for example, reduce or prevent induction of current from external electromagnetic sources. Conventional electrical stimulation systems may be potentially unsafe for use with magnetic resonance imaging ("MRI") due to the effects of electromagnetic fields, such as the RF and varying magnetic fields, in an MM environment. A common mechanism for electrical interactions between the electrical stimulation system and RF irradiation is common-mode coupling of the external electromagnetic fields that act as a series of distributed sources along the conductors within leads. Common-mode induced RF currents can reach amplitudes of greater than one ampere in Mill environments. Some of the effects of the external electromagnetic may include, for example, inducing current in the lead; causing undesired heating of the lead that may potentially cause tissue damage; undesired or unexpected operation of electronic components; or premature failure of electronic components.

Conductors within the modular lead element can be arranged into one or more coiled geometries along the length of the conductors to eliminate or reduce the effect of external electromagnetic fields. As herein described, the conductors extending along the length of the lead may include one or more coiled regions having geometries. The coiled regions can be disposed along the entire length of the conductors, or one or more portions thereof. Additionally, the coiled geometry can be changed along the length of the modular lead element in either a continuous or a discontinuous manner.

In at least some embodiments, the coiled conductors may be arranged in one or more suppression units within the modular lead element. Examples of electrical stimulation systems with leads having conductors formed into suppression units are found in, for example, U.S. Patent Application Publication Nos. 2010/0076508; 2010/0094364; and 2010/0256693; 2010/0326701; 2011/0009932; 2011/0046700, all of which are incorporated herein by reference.

Figure 5:
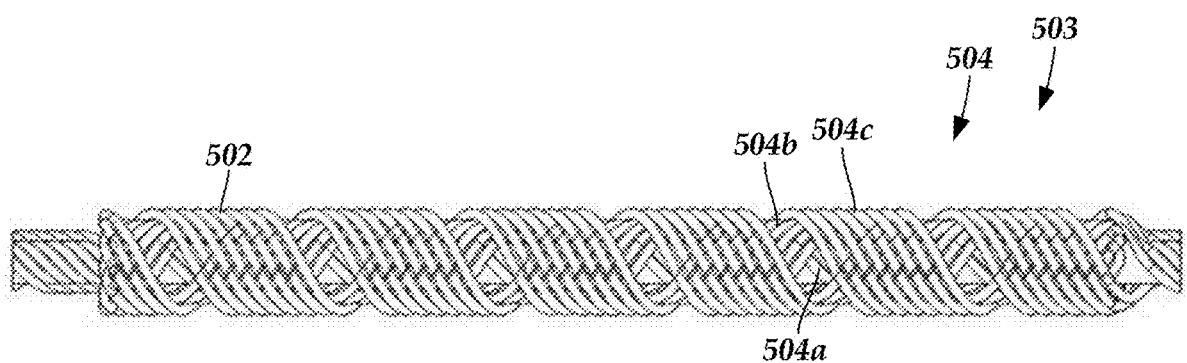
FIG. 5 is a schematic side view of one embodiment of a conductor arrangement for a modular lead element.

FIG. 5 schematically illustrates one embodiment of a plurality of conductors 502 forming at least one suppression unit 504. Each suppression unit includes a first conductor segment 504*a*, a second conductor segment 504*b*, and a third conductor segment 504*c*. In at least some embodiments, the three conductor segments 504*a*, 504*b*, 504*c* at least partially overlap one another to form a multi-layer region.

The first conductor segment 504*a* extends in a first direction along a longitudinal length of the modular lead element from a beginning point to a first position. A second conductor segment 504*b* extends from the first position back towards (and possibly past) the beginning point to a second position. The third conductor segment 504*c* extends in the first direction from the second position to an endpoint. In at least some embodiments, the first position is between the second position and the endpoint. In at least some embodiments, the second position is between the beginning point and the first position. In at least some embodiments, the suppression unit may include a single-layer region flanking at least one end of the multi-layer region.

The suppression units may be electrically continuous such that the endpoint of one suppression unit is the beginning point of the next consecutive suppression unit. At least one of the beginning points for the series of suppression units may be a contact, an electrode, or a terminal. Likewise, at least one of the endpoints for the series of units may be a contact, an electrode, or a terminal. In at least some embodiments, one, two, or three of the conductor segments are each coiled. In at least some embodiments, the conductor segments are coiled around a liner. In at least some embodiments, the liner defines a lumen that optionally is configured and arranged to receive a stylet or the like). In at least some embodiments, at least one of the first, second, or third conductor segments is straight. In at least some embodiments, the first and third conductor segments are straight and the second conductor segment is coiled.

Any suitable number of suppression units may be disposed along the high impedance modular lead element including, for example, one, two, three, four, five, six, seven, eight, nine, ten, twelve, twenty, or more suppression units. It will be understood that many other numbers of units may be employed as well.

In at least some embodiments, a high impedance modular lead element can include the conductors arranged so that, starting from the proximal end portion, the conductors extend along the modular lead element from the proximal end portion to the distal end portion with at least one reversal of direction back towards the proximal end portion followed by a resumption in the direction towards the distal end portion. These conductors may be straight, twisted, or coiled or any combination thereof.

A lead can be formed using any number of modular lead elements including, but not limited to, two, three, four, five, six, seven, eight or more modular lead elements. A lead can include any number of low impedance modular lead elements including, but not limited to, one, two, three, four, five, or more low impedance modular lead elements. A lead can include any number of high impedance modular lead elements including, but not limited to, one, two, three, four, five, or more high impedance modular lead elements. A lead can include both low and high impedance modular lead elements including, but not limited to, one, two, three, four, five, or more low impedance modular lead elements and one, two, three, four, five, or more high impedance modular lead elements. In at least some embodiments, a lead can include at least two low impedance modular lead elements and at least one high impedance modular lead element.

Any arrangement of low impedance modular lead elements and high impedance modular lead elements can be used. For example, a lead may include low impedance modular lead elements at both the distal and proximal ends of the lead and a high impedance modular lead element therebetween. As another example, a lead may include a low impedance modular lead element at the distal end with a high impedance module lead element directly proximal to that low impedance module lead element. Optionally, the lead may include one or more additional high impedance modular lead elements or low impedance modular lead elements or any combination thereof.

The selection and arrangement of the low impedance modular lead elements and high impedance modular lead elements can be based on any suitable considerations. For example, the selection and overall lead length may be tailored to the patient, the desired implantation site, the desired stimulation site, the desired site of the control module, or any combination thereof. In at least some embodiments, the selection and arrangement and lead length may be selected during or prior to the lead implantation surgery.

High impedance modular lead elements may be selected for use along the lead based on anatomy. For example, high impedance modular lead elements may be placed along the lead near regions that are less susceptible to heat or fatty tissues or near neural tissues (for example, one or two lead elements positioned directly proximal to the lead element containing the electrodes.) A high impedance modular lead element may be positioned directly distal to the lead element containing the terminals to reduce or curtail RF induced voltage or current into the control module. High impedance modular lead elements may be positioned immediately proximal to size restricted anatomical regions (such as the entry into the skull or the foramen/sacrum in the spine) as the high impedance modular lead elements may be larger in diameter.

The use of modular lead elements can also facilitate tailoring the array of electrodes or array of terminals. For example, if there is an obstruction or other anatomical need, the clinician may alter the distal array of electrodes by switching out the distal-most modular lead element. In some embodiments, a proximal-most modular lead element with the array of terminals may be selected or change to match the selected control module. Such changes may facilitate making the leads forward or backward compatible to existing or future control modules or control modules from different manufacturers. Similarly, the modular arrangement may facilitate implanting an isodiametric portion of a lead through a needle, cannula, or other introducer and then attaching a modular lead element that includes two or more proximal lead bodies (for example, a modular lead element that is bifurcated into two proximal tails) that each include an array of terminals. Modular lead elements may also facilitate upgrading to new technologies such as in-line multiplexing or the inclusion of optical stimulation.

Figure 6:
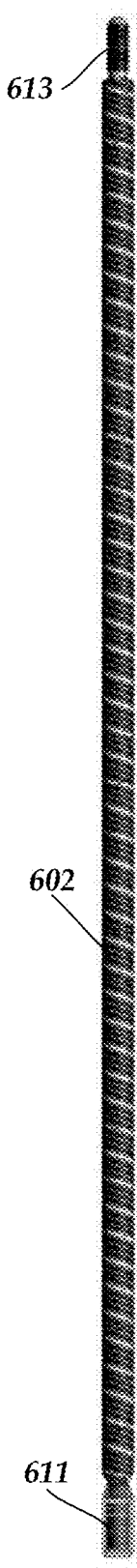
FIG. 6 is a schematic side view of one embodiment of a modular lead element.

As described above, each of the modular lead elements includes at least one female connector element or male connector element. The modular lead elements are coupled together by inserting a male connector element into a female connector element. FIG. 6 illustrates one embodiment of a portion of a high impedance modular lead element 630 with a female connector element 611 at one end and a male connector element 613 at another end. In at least some embodiments, the conductors 602 of the high impedance modular lead element 630 are covered with a non-conductive jacket when complete.

Figure 7:
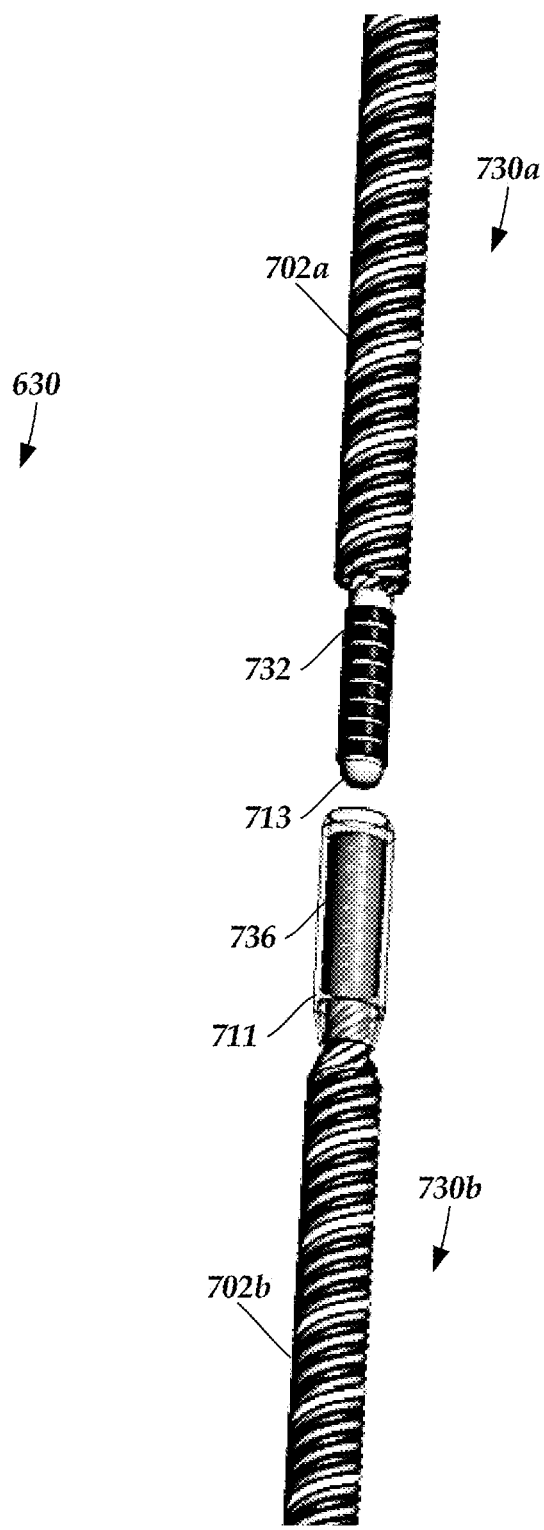
FIG. 7 is a schematic side view of one embodiment of the portions of two modular lead elements with a female connecter element and a male connector element, respectively.

FIG. 7 illustrates portions of two high impedance modular lead elements 730a, 730b. The high impedance modular lead element 730a includes a male connector element 713 with contacts 732 disposed along the male connector element. The conductors 702a of the high impedance modular lead element 703a are individually, electrically coupled to the contacts 732. As an example, each conductor 702a can be electrically coupled to a different one of the contacts 732. Similarly, a low impedance modular lead element may include a male connector element with contacts and the conductors of the low impedance modular lead element electrically coupled to the contacts of the male connector element.

The high impedance modular lead element 730b includes a female connector element 711 defining a lumen 734 for receiving the male connector element 713. Contacts 736 disposed within the female connector element 711 along the lumen 734. The conductors 702b of the high impedance modular lead element 703b are individually, electrically coupled to the contacts 736. As an example, each conductor 702b can be electrically coupled to a different one of the contacts 736. Similarly, a low impedance modular lead element may include a female connector element with a lumen and contacts and the conductors of the low impedance modular lead element electrically coupled to the contacts of the female connector element.

Figure 8:
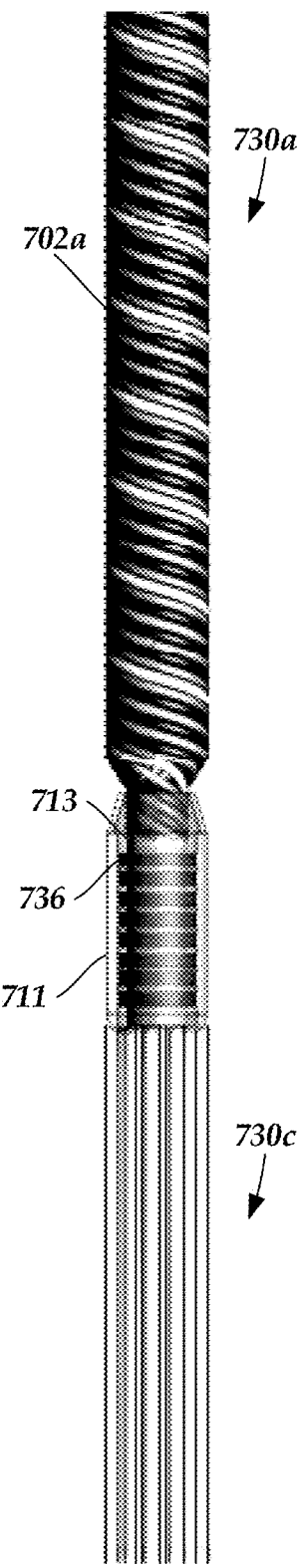
FIG. 8 is a schematic side view of another embodiment of the portions of two modular lead elements mated together.

The male connector element 713 and female connector element 711 are arranged to mate the contacts 732 of the male connector element 713 with the contacts 736 of the female connector element 711. FIG. 8 illustrates a high impedance modular lead element 730a mated with a low impedance modular lead element 730c. In this illustrated embodiment, the low impedance modular lead element 730c includes the male connector element 713 and the high impedance modular lead element 730a includes the female connector element 711.

Any suitable type of male and female connector elements can be used to connect the modular lead elements together. The contacts 732, 736 of the connector elements 711, 713 can be any suitable contacts including, but not limited to, contact rings, canted coil contacts (such as those available from Bal Seal Engineering (Foothills Ranch, Calif.), spring contacts, wire contacts, or the like.

In some embodiments, the male and female connector elements may include a fastener, such as a screw, pin, or the like, to fasten the connector elements when mated. In some embodiments, the male and female connector elements may be fastened together by welding, soldering, adhesive, or the like. In some embodiments, the male and female connector elements may be form, or include features that form, a compression fit or interference fit to hold the connector elements together.

In at least some embodiments, as illustrated in FIGS. 6-8, a male connector element 613, 713 has an outer diameter that is smaller than an outer diameter of the modular lead element 630, 730*a-c* exclusive of the male and female connector elements. In at least some embodiments, as illustrated in FIGS. 6-8, a female connector element 611, 711 has an outer diameter that is no greater than (and, in some embodiments, less than) an outer diameter of the modular lead element 630, 730*a-c* exclusive of the male and female connector elements. Such arrangements may limit the maximum outer diameter or bulk of the modular lead to be comparable to that of a non-modular lead. It will be understood, however, that other arrangements with outer diameters of one or both of the male or female connector elements being larger than the outer diameter of the modular lead element exclusive of the male and female connector elements are also possible.

Figure 9A:
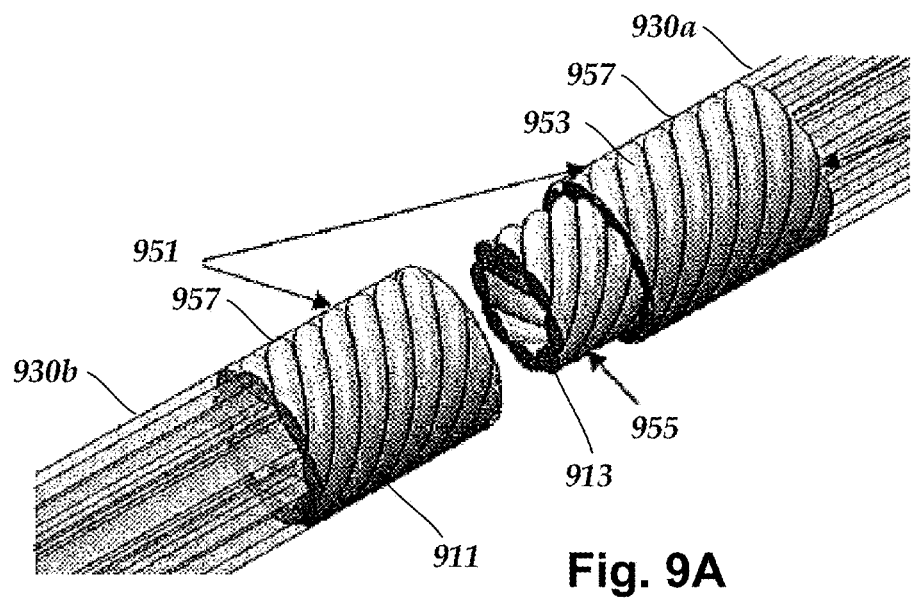
FIG. 9A is a schematic perspective view of one embodiment of a male connector element and a female connector element prior to mating.
Figure 9B:
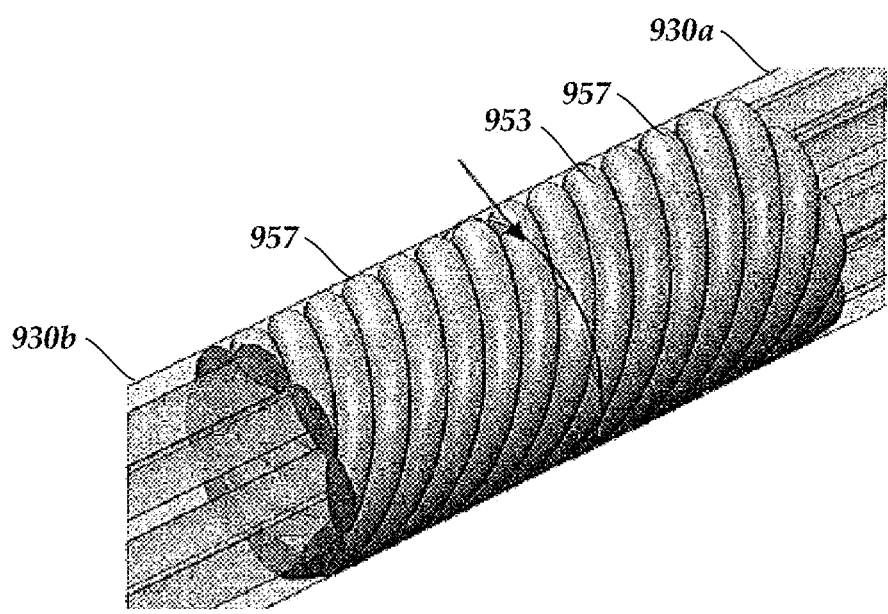
FIG. 9B is a schematic side view of the male and female connector elements of FIG. 9A mated together.

FIGS. 9A and 9B illustrate one embodiment of a male connector element 913 and female connector element 911 at respective ends of low impedance modular lead elements 930*a*, 930*b*. These connector elements 911, 913 can also be used with high impedance modular lead elements.

In one embodiment, the male connector element 913 and female connector element 911 are formed of helical hollow strand (HHS™) tube 951. The male connector element 913 forms an inner helix 955 of tubes 953 and both the male connector element 913 and the female connector element 911 form an outer helix 957 of tubes 953. The tubes 953 of the outer helices 957 are preferably insulated from each other and individual tubes of the outer helices are electrically coupled to the conductors in the respective low impedance modular lead element 930*a*, 930*b*. The inner helix 955 acts as a threaded screw and screws into the outer helix 957 of the female connector element 911. The corresponding tubes 953 of the outer helices 957 of the male connector element 913 and female connector element 911 can make electrical contact or welded or soldered together to form electrical connection between the two modular lead elements 930*a*, 930*b*. Optionally, when connected together, as illustrated in FIG. 9B, the male and female connector elements 911, 913 can be overmolded with plastic.

As another example, instead of HHS tubes, the outer helices 957 (and optionally the inner helix 955) can be made of plastic tubes with the conductors of the respective modular lead elements 930*a*, 930*b* extending through the plastic tubes of the outer helices. These conductors can be welded or soldered together prior to, or during assembly, and then the male connector element 913 and female connector element 911 mated.

Figure 10:
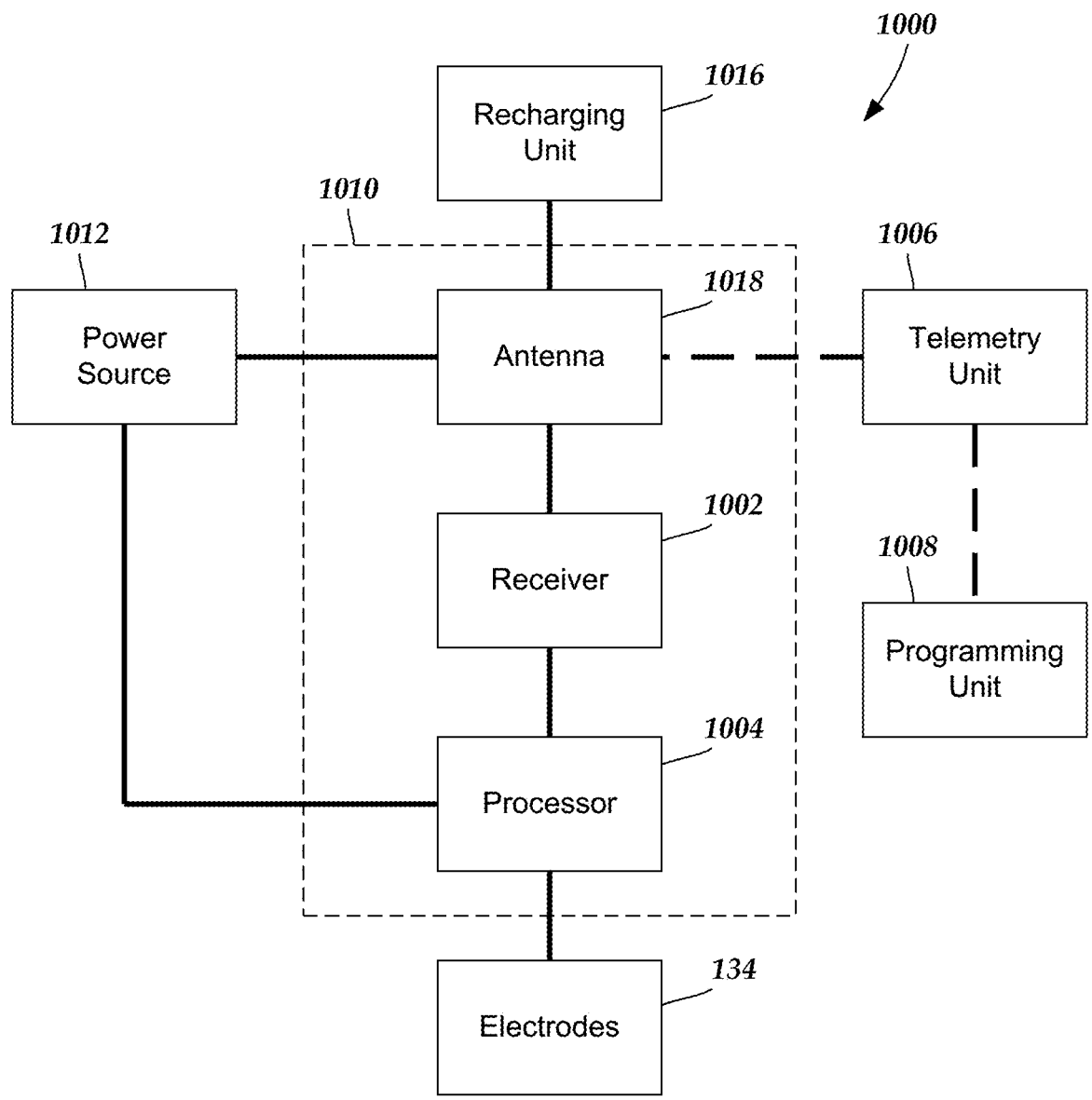
FIG. 10 is a schematic overview of one embodiment of components of a stimulation system, including an electronic subassembly disposed within a control module.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead, comprising:
at least three modular lead elements configured to couple together to form the implantable electrical stimulation lead, each of the modular lead elements comprising a proximal end portion, a distal end portion, and a male connector element or a female connector element disposed on at least one of the proximal end portion or the distal end portion of the modular lead element, wherein the modular lead elements collectively comprise a plurality of the male connector elements and a plurality of the female connector elements, wherein the modular lead elements are coupleable together by insertion of a one of the male connector elements into a one of the female connector elements, wherein each of the modular lead elements comprises contacts disposed on each male connector element or within each female connector element of the modular lead element and conductors extending along the modular lead element from the contacts,
wherein the at least three modular lead elements comprises two first modular lead elements and one second modular lead element, wherein the implantable electrical stimulation lead is arranged so that the second modular lead element is only coupleable at a position along the implantable electrical stimulation lead that is between the two first modular lead elements,
wherein the conductors of the two first modular lead elements are disposed in a low impedance arrangement, and
wherein the conductors of the second modular lead element are disposed in a high impedance arrangement, wherein the high impedance arrangement of the conductors forms at least one suppression unit, wherein each of the at least one suppression unit comprises a first conductor segment extending in a first direction along a longitudinal length of the second modular lead element from a beginning point to a first position; a second conductor segment extending from the first position in a second direction, opposite the first direction, to a second position; and a third conductor segment extending in the first direction from the second position to an endpoint.

2. The implantable electrical stimulation lead of claim 1, wherein the low impedance arrangement of the conductors comprises the conductors extending along the first modular lead element in either a straight configuration or a twisted configuration with twisting of the conductors at a rate of no more than one turn per centimeter.

3. The implantable electrical stimulation lead of claim 1, wherein each of the female connector elements has an outer diameter no greater than an outer diameter of a one of the modular lead elements of which the female connector element is part.

4. An electrical stimulation system, comprising
the implantable electrical stimulation lead of claim 1; and
a control module coupleable to the implantable electrical stimulation lead and comprising a housing and an electronic subassembly disposed in the housing and electrically coupleable to the implantable electrical stimulation lead.

5. A method of making the implantable electrical stimulation lead of claim 1, the method comprising
coupling the at least three modular lead elements together by inserting the female connector elements into the male connector elements.

6. The method of claim 5, wherein coupling the at least three modular lead elements comprises at least one of:
i) coupling the second modular lead element with conductors in the high impedance arrangement immediately proximal to a one of the modular lead elements comprising a plurality of electrodes;
ii) coupling the second modular lead element with conductors in the high impedance arrangement immediately distal to a one of the modular lead elements comprising a plurality of terminals;
iii) coupling the second modular lead element with conductors in the high impedance arrangement immediately proximal to a one of the modular lead elements that is arranged for insertion through a size-restricted anatomical region;
iv) coupling the second modular lead element with conductors in the high impedance arrangement at a position along the implantable electrical stimulation lead intended for implantation adjacent to neural tissue; or
v) coupling the second modular lead element with conductors in the high impedance arrangement at a position along the implantable electrical stimulation lead intended for implantation adjacent to fatty tissue.

7. The implantable electrical stimulation lead of claim 1, wherein the at least three modular lead elements comprises two of the second modular lead elements with the two of the second modular lead elements coupled to each other and disposed at a position along the implantable electrical stimulation lead between the two first modular lead elements.

8. An implantable electrical stimulation lead, comprising:
at least three modular lead elements configured to couple together to form the implantable electrical stimulation lead, each of the modular lead elements comprising a proximal end portion, a distal end portion, and a male connector element or a female connector element disposed on at least one of the proximal end portion or the distal end portion of the modular lead element, wherein the modular lead elements collectively comprise a plurality of the male connector elements and a plurality of the female connector elements, wherein the modular lead elements are coupleable together by insertion of a one of the male connector elements into a one of the female connector elements, wherein each of the modular lead elements comprises contacts disposed on each male connector element or within each female connector element of the modular lead element and conductors extending along the modular lead element from the contacts, wherein the conductors of at least one of the modular lead elements are disposed in a low impedance arrangement, and wherein the conductors of at least one of the modular lead elements are disposed in a high impedance arrangement, wherein each of the female connector elements comprises an outer helix of tubes and each of the male connector elements comprises an outer helix of tubes and an inner helix of tubes, wherein the inner helix of tubes is configured to screw into the outer helix of tubes of a one of the female connector elements to mate the one of the female connector elements to a one of the male connector elements.

9. The implantable electrical stimulation lead of claim 8, wherein the high impedance arrangement of the conductors extending along the modular lead element is a coiled configuration with a coil pitch of more than one turn per centimeter.

10. The implantable electrical stimulation lead of claim 8, wherein the high impedance arrangement of the conductors forms at least one suppression unit.

11. The implantable electrical stimulation lead of claim 10, wherein each of the at least one suppression unit comprises a first conductor segment extending in a first direction along a longitudinal length of the modular lead element from a beginning point to a first position; a second conductor segment extending from the first position in a second direction, opposite the first direction, to a second position; and a third conductor segment extending in the first direction from the second position to an endpoint.

12. The implantable electrical stimulation lead of claim 8, wherein the at least three modular lead elements comprises a first modular lead element comprising a plurality of terminals disposed along the proximal end portion, a first male connector element or a first female connector element disposed on the distal end portion, and conductors extending from the terminals to the contacts of the first male connector element or the first female connector element, a second modular lead element comprising a plurality of electrodes disposed along the distal end portion, a second male connector element or a second female connector element disposed on the proximal end portion, and conductors extending from the electrodes to the contacts of the second male connector element or the second female connector element, and a third modular lead element comprising a third male connector element or a third female connector element disposed along the distal end portion, a fourth male connector element or a fourth female connector element disposed on the distal end portion, and conductors extending from the contacts of the third male connector element or the third female connector element to the contacts of the fourth male connector element or the fourth female connector element.

13. The implantable electrical stimulation lead of claim 12, wherein the third modular lead element has the conductors disposed in the high impedance arrangement and the first and second modular lead elements have the conductors disposed in the low impedance arrangement.

14. An implantable electrical stimulation lead, comprising:

at least three modular lead elements configured to couple together to form the implantable electrical stimulation lead, each of the modular lead elements comprising a proximal end portion, a distal end portion, and a male connector element or a female connector element disposed on at least one of the proximal end portion or the distal end portion of the modular lead element, wherein the modular lead elements collectively comprise a plurality of the male connector elements and a plurality of the female connector elements, wherein the modular lead elements are coupleable together by insertion of a one of the male connector elements into a one of the female connector elements, wherein each of the modular lead elements comprises contacts disposed on each male connector element or within each of the female connector element of the modular lead element and conductors extending along the modular lead element from the contacts, wherein the at least three modular lead elements comprises two first modular lead elements and one second modular lead element, wherein the implantable electrical stimulation lead is arranged so that the second modular lead element is only coupleable at a position along the implantable electrical stimulation lead that is between the two first modular lead elements, wherein the conductors of the two first modular lead elements have a first conductor arrangement in which, starting from the proximal end portion, the conductors extend along the first modular lead element from the proximal end portion to the distal end portion without reversing direction back towards the proximal end portion, and wherein the conductors of the second modular lead element have a second conductor arrangement in which, starting from the proximal end portion, the conductors extend along the second modular lead element from the proximal end portion to the distal end portion with at least one reversal of direction back towards the proximal end portion followed by a resumption in the direction towards the distal end portion.

15. The implantable electrical stimulation lead of claim 14, wherein the at least three modular lead elements comprises a one of the two first modular lead elements comprising a plurality of terminals disposed along the proximal end portion, a first male connector element or a first female connector element disposed on the distal end portion, and conductors extending from the terminals to the contacts of the first male connector element or the first female connector element, another one of the two first modular lead elements comprising a plurality of electrodes disposed along the distal end portion, a second male connector element or a second female connector element disposed on the proximal end portion, and conductors extending from the electrodes to the contacts of the second male connector element or the second female connector element, and a third modular lead element comprising a third male connector element or a third female connector element disposed along the distal end portion, a fourth male connector element or a fourth female connector element disposed on the distal end portion, and conductors extending from the contacts of the third male connector element or the third female connector element to the contacts of the fourth male connector element or the fourth female connector element.

16. The implantable electrical stimulation lead of claim 15, wherein the third modular lead element has the conductors in the second conductor arrangement.

17. The implantable electrical stimulation lead of claim 14, wherein the second conductor arrangement forms at least one suppression unit.

18. The implantable electrical stimulation lead of claim 14, wherein each of the at least one suppression units comprises a first conductor segment extending in a first direction along a longitudinal length of the modular lead element from a beginning point to a first position; a second conductor segment extending from the first position in a second direction, opposite the first direction, to a second position; and a third conductor segment extending in the first direction from the second position to an endpoint.

19. An electrical stimulation system, comprising
the implantable electrical stimulation lead of claim 14; and
a control module coupleable to the implantable electrical stimulation lead and comprising a housing and an electronic subassembly disposed in the housing and electrically coupleable to the implantable electrical stimulation lead.

20. A method of making the implantable electrical stimulation lead of claim 14, the method comprising
coupling the at least three modular lead elements together by inserting the female connector elements into the male connector elements.

* * * * *